US005991019A

United States Patent [19]

Sander et al.

[11] Patent Number: 5,991,019

[45] Date of Patent: Nov. 23, 1999

[54] METHOD AND APPARATUS FOR BUBBLE CHAMBER SPECTROSCOPY

[75] Inventors: Robert K. Sander, Los Alamos; Jerry H. Atencio, Espanola; Edward I. McCreary; Xin Luo, both of Los Alamos, all of N.Mex.

[73] Assignee: Regents of the University of California, Los Alamos, N.Mex.

[21] Appl. No.: 08/627,833

[22] Filed: Apr. 2, 1996

[51] Int. Cl.$^{6}$ .............................. G01J 3/00; G01N 21/00

[52] U.S. Cl. .............................................................. 356/300

[58] Field of Search .................................... 356/300, 317, 356/318

[56] References Cited

PUBLICATIONS

G. Harigel, et al., On the Formation of Narrow Bubble Tracks by A Laser Beam in Argon, Nitrogen and Hydrogen Bubble Chambers, Apr. 3, 1996, Geneva, Switzerland.

R.C. Stamberg, et al, "Laser–Stimulated Nucleation in a Bubble Chamber," Mar. 15, 1996 and Aug. 16, 1965, Univ. of Michigan, Ann Arbor, Michigan.

R.A. Leach, et al., "Thermal Lens Absorption Measurements by Flow Injection into Supercritical Fluid Solvents," 1984, Dept. of Chemistry, Univ. of Utah, Salt Lake City, Utah.

Jerry H. Atencio, et al., "Abstract and Bubble Chamber Spectroscopy," 150/SPIE vol. 2385, Los Alamos National Lab, Los Alamos, New Mexico.

*Primary Examiner*—F. L. Evans
*Attorney, Agent, or Firm*—Ray G. Wilson

[57] ABSTRACT

A bubble chamber spectrometer provides a new method for the sensitive detection of an analyte in a solvent. A bubble chamber receives a solution containing an analyte to be detected. A laser is adapted to direct an output laser beam through the bubble chamber, where the laser is selected to be absorbed by the analyte and to be transmitted by the solvent. A video camera is adapted to display passage of said laser beam through said bubble chamber so that bubbles in the solvent arising from energy deposition in the analyte can be counted to characterize the analyte both quantitatively and qualitatively.

7 Claims, 5 Drawing Sheets

METHOD AND APPARATUS FOR BUBBLE CHAMBER SPECTROSCOPY

BACKGROUND OF THE INVENTION

This invention relates to sensing small amounts of selected materials, and, more particularly, to the application of optical absorption spectroscopy to sensing small amounts of materials. This invention was made with government support under Contract No. W-7405-ENG-36 awarded by the U.S. Department of Energy. The government has certain rights in the invention.

There are many applications for the detection of trace quantities of materials in solutions. For example, ultrasensitive analysis requirements exist in forensic applications, intelligence gathering, and biomedical analysis. Artificial nanoparticles may be used as tracers in environmental research or as labels for chemical analysis. Large labeled molecules are used in DNA identification, protein identification, and tracking man-made polymers. In addition, quality control applications particularly include material purity determinations in the semiconductor industry, pharmaceuticals, and in refrigerant chemicals.

There are sensitive detection techniques available, but each has some limitation, i.e., limited sensitivity, limited feature for detection, cost, and the like. Mass spectroscopy is very sensitive to small quantities of materials but it is inherently a gas phase or vacuum-based technique. A complex interface is needed with solid or liquid samples and that interface can introduce losses from the samples. Solution-based samples are output from a number of analytical methods, e.g., electrophoresis and liquid chromatography. It is desirable for an analytical tool to be able to access materials in solution rather than require the sample in a gas phase.

Fluorescence techniques are quite sensitive and can be used on liquid samples. But the technique is limited to only the relatively small number of molecular species that fluoresce with high efficiency. Photothermal and photoacoustic techniques are applicable to liquid samples with an analyte that absorbs light, but the technique is not as sensitive as fluorescence spectroscopy and is not useful in some applications.

The present invention overcomes the above problems and a bubble chamber is adapted for spectroscopic analyses. Accordingly, it is an object of the present invention to provide a highly sensitive analytical technique that is useful with liquid solutions of small quantities of analyte.

Another object of the present invention is to provide a spectroscopic technique that is relatively insensitive to environmental noise.

Yet another object of the present invention is to provide a spectroscopic technique that is useful with a wide variety of analytes.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise a bubble chamber spectrometer. A bubble chamber receives a solution containing an analyte to be detected. A laser is adapted to direct an output laser beam through the bubble chamber, where the laser is selected to be absorbed by the analyte and to be transmitted by the solvent. A video camera is adapted to display passage of said laser beam through said bubble chamber so that bubbles in the solvent arising from energy deposition in the analyte can be counted to characterize the analyte both quantitatively and qualitatively.

In another characterization of the presentation, a method for bubble chamber spectroscopy provides a sensitive detection system for analyte in a solution. A solution containing an analyte is passed into a bubble chamber. The pressure in the bubble chamber is reduced to create a superheated liquid. The solvent and the analyte are illuminated with a laser to deposit energy in the analyte so that deposited energy in the analyte causes solvent adjacent the analyte to form bubbles. The resulting bubbles are then counted to characterize the solution.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Figure 1:
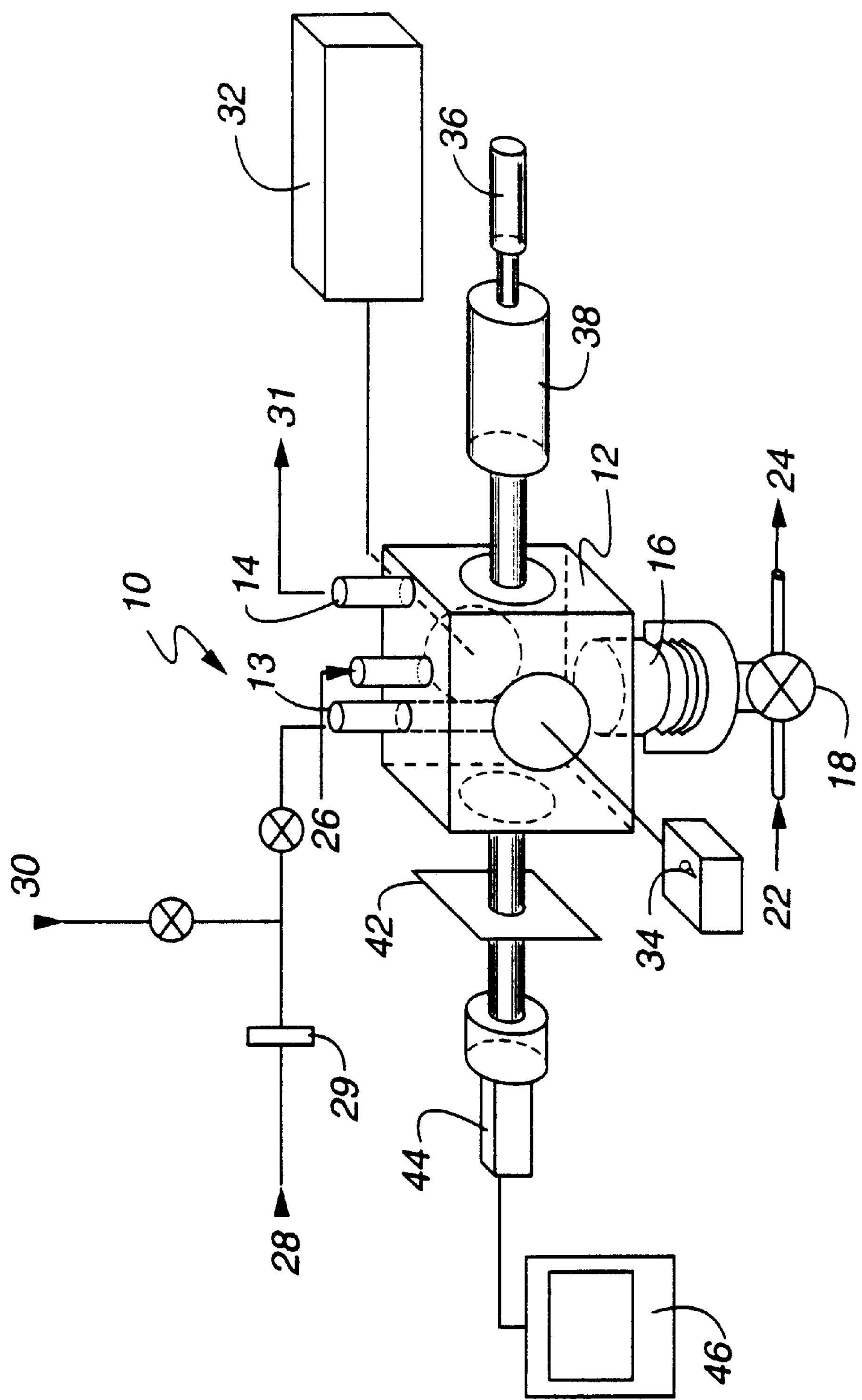
FIG. 1 is a pictorial illustration of a bubble chamber spectrometer according to one embodiment of the present invention.

In accordance with the present invention, a bubble chamber is adapted for use as a bubble chamber spectrometer that can be used to identify and quantify an analyte in a solution. FIG. 1 illustrates a bubble chamber spectrometer 10 according to one embodiment of the present invention. A conventional bubble chamber 12 is provided with inlet 13 and outlet 14 for introducing and removing a solvent carrying an analyte. A high energy pulsed light source 32, preferably a laser, is adapted through conventional optics (not shown) to direct a light beam through bubble chamber 12. Energy meter 34 may be provided to measure the energy of the light beam transmitted through bubble chamber 12. Energy in the light beam is deposited within bubble chamber 12, as discussed below, to cause the nucleation and growth of bubbles within chamber 12.

A conventional bubble chamber employs the principle that high energy particles passing through a metastable superheated liquid transfer some part of their energy into the fluid and initiate phase transitions along the particle trajectory. The key to bubble formation in these fluids is an energy deposition intense enough for localized heat transfer to induce a phase transition and create a small "pocket" of gas for the internal pressure to overcome the compressive force of the surrounding fluid. Since the surface tension of the surrounding fluid will tend to compress these gas pockets, bubbles can grow only if sufficient energy is absorbed to create enough gas for the internal pressure to overcome the compressive force of the surface tension. Nucleation centers larger than a critical size will grow spontaneously through evaporation of the superheated liquid.

It is known that a light beam propagating through such a superheated fluid in a bubble chamber demonstrates similar effects when the energy in the light beam is deposited in the fluid. See, e.g., R. C. Stamberg et al., "Laser-Stimulated Nucleation in a Bubble Chamber," 37 J. Applied Phys., pp. 459–461 (1966) and G. Harigel et al., "On the Formation of Narrow Bubble Tracks by a Laser Beam in Argon, Nitrogen, and Hydrogen Bubble Chambers," 188 Nuclear Instruments and Methods, pp. 517–520. In this instance, a sudden mechanical release of pressure on the system provides a liquid in a superheated state and energy is deposited into the fluid through absorption excitation, i.e., absorption of the light energy by one or more substances forming the fluid. The radiationless relaxation of the excited superheated liquid and impurities induces phase transitions and creates nucleation centers through localized heating. Preferential boiling from these nucleation centers precedes wall nucleated boiling, making possible the differentiation of bubbles along the light path.

In accordance with the present invention, it is recognized that the above characteristics of a bubble chamber enable the bubble chamber to serve as a spectrometer where the presence of trace amounts of an analyte can be distinguished from bubble tracks produced through a solvent carrying the analyte through the bubble chamber. As shown in FIG. 1, bellows 16 provides a pulsed release of pressure on the liquid within bubble chamber 12 necessary to create a superheated liquid and the concomitant growth of nucleation centers to observable bubbles. A solution is input to bubble chamber 12 by combining a solvent introduced through input line 28 and filter 29 and an analyte introduced through line 30. Filter 29 is selected to remove particulate impurities in the solvent. The resulting solution is output through output line 31. Bellows 16 is compressed by high pressure gas 22 to pressurize a solution within chamber 12. This pressure keeps the liquid from boiling in its normal state of operation. The pressure in bubble chamber 12 may be detected by pressure transducer 26. A metastable fluid condition is established through rapid release of the pressure in bellows 16 by actuating solenoid valve 18 to exhaust the pressurizing gas through exhaust line 24. Light from light source 32 is absorbed by one or more materials within bubble chamber 12 to create a nucleation center.

As bubbles form along the path of the light beam, the bubbles are illuminated by a low power light source, which may be a diode laser 36 having a beam width expanded through optics 38. Transmitted light from laser 36 is preferably passed through a suitable filter 42 to remove "noise" and scattered light and is then received by camera 44. Camera 44 may be any one of a number of types of video camera to form an image of the bubbles, but a preferred form of camera 44 is a charge coupled device having an output that is readily adapted for counting the number of bubbles within a video frame. The output from camera 44 is provided to an information processor 46, which may be a general purpose computer that is programmed to capture a frame of data, analyze the frame for the presence of bubbles, count the bubbles and then to assimilate and correlate the various parameters in the system to graphically present the system output.

Figure 2:
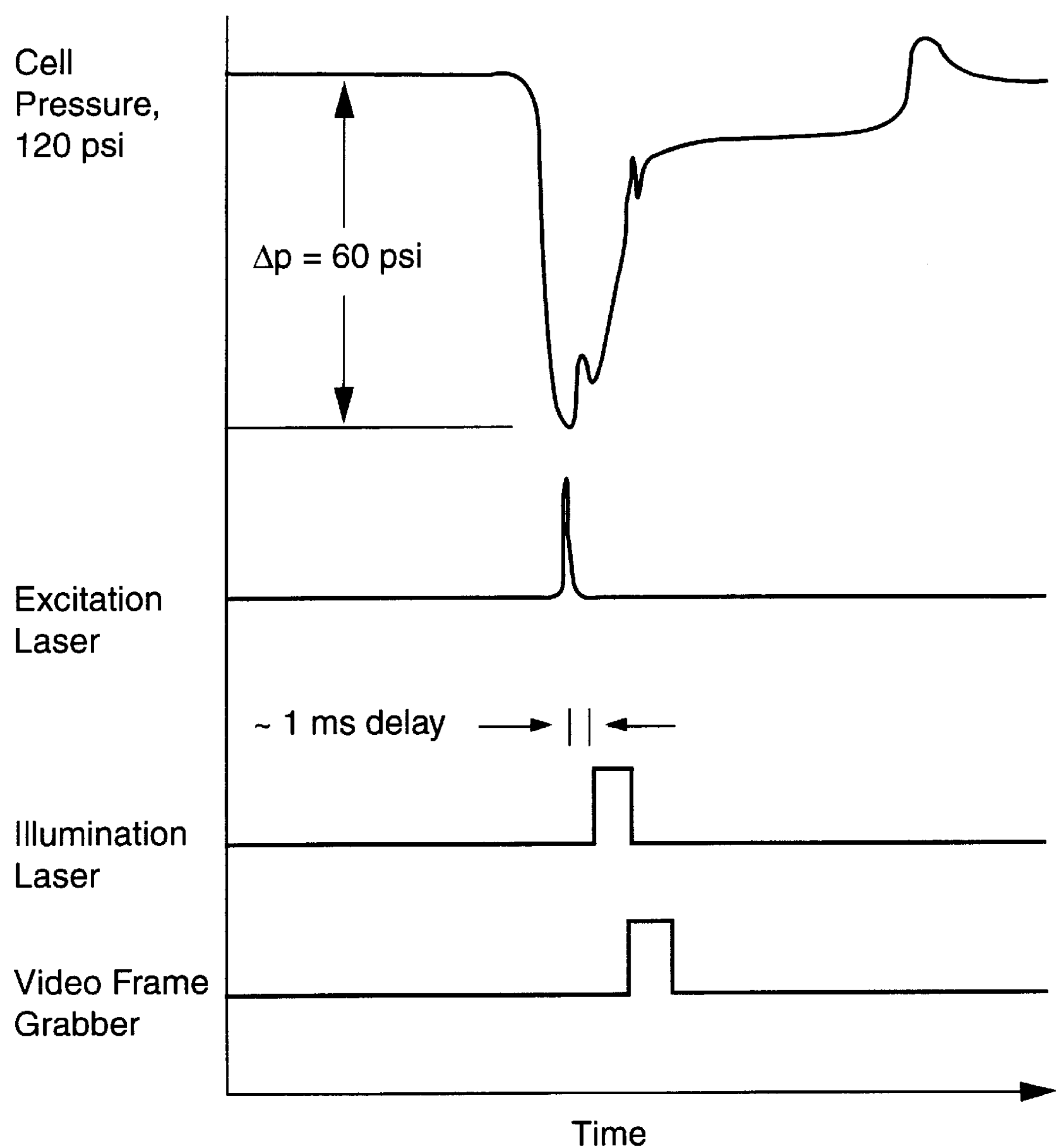
FIG. 2 illustrates the temporal relationship of various components of the spectrometer shown in FIG. 1.

FIG. 2 graphically depicts the operation of the bubble chamber spectrometer described. A solvent is introduced under pressure into the bubble chamber. For example, liquid propane normally boils at −30° C.; at room temperature its vapor pressure is 120 pounds per square inch. When the pressure is reduced, the propane enters a temporary superheated state. A laser beam is then directed into the solvent, where the specific color or wavelength of the laser is determined by the absorption characteristics of the analyte to be examined and is selected away from any absorbance of the solvent. Thus, the solvent is normally transparent to the selected laser beam so that no energy is absorbed, although impurities in the solvent may absorb a small amount of energy.

In the presence of an analyte, however, laser energy is absorbed, causing nucleation centers to form and bubbles to grow in the path of the laser beam. The original nucleation center is invisibly small (on the molecular scale), but the rapid growth of the bubble in the superheated liquid makes it visible to the camera that is directed perpendicular to the laser beam. The bubble growth is illuminated a short time after the laser pulse and the video camera is activated thereafter to capture images of bubble growth. The number of bubbles is determined by a conventional image analysis algorithm as a measure of the number of the light-absorbing analyte particles in the solvent. The algorithm can restrict the count of bubbles to specific portions of the image to avoid bubbles produced outside of the path illuminated by the light beam. After a measurement, the solvent is pressurized again to prepare for another cycle. The cycles can be repeated in about 5 seconds.

In a demonstration of the present invention, a bubble chamber was formed of a small six way stainless steel cube (20 mL interior volume) modified to hold four quartz windows in the vertical faces. The bottom face had a flexible stainless steel bellows compressed by application of pressurized nitrogen (120–160 psi) modulated with a solenoid valve and the chamber was filled through piping in the top face. Pressure pulse width and amplitude are varied by changes in gas pressure and driving voltage applied to the solenoid valve. The pressure pulse shape was monitored by a pressure transducer on the top face of the chamber. A typical pressure pulse had a 8 msec FWHM (full width half maximum) over a 50–60 psi drop. A low duty cycle of 0.2 Hz enabled the system to return to equilibrium before each measurement.

High purity research grade propane (available from Matheson) was used without further purification as the solvent. The propane was passed through two filters (0.5 $\mu$m and 0.02 $\mu$m) to remove particulate impurities. Propane has a low absorption cross-section for visible and near-UV light and has a modest vapor pressure of 110 psi at room temperature to permit operation of the bubble chamber without pressure concerns or extreme temperature concerns. Propane is also a sufficiently strong solvent to keep most organic compounds in solution.

Analyte materials were diluted in spectroscopic grade acetone and injected into a 20 $\mu$L storage loop. Propane flow into the bubble chamber is diverted through the loop and the sample was then directed into the chamber and the chamber was allowed to come to thermal equilibrium at room temperature (25° C.). Pulsing the solenoid valve allowed the bellows to expand under pressure from the propane. Some 30 ms after the trigger pulse to the solenoid occurred and at the minimum of the pressure pulse in the cell before wall nucleated boiling occurred, the pump laser beam was directed through the bubble chamber. An exemplary pump laser is a frequency doubled Nd:Yag (532 nm) laser with a 10 ns pulse width and focused to a 2 mm beam waist in the bubble chamber. Beam energy, as measured at an exit window of the bubble chamber was varied from 30 μJ to 3 mJ. An example of another suitable laser is a Nd:YAG pumped barium borate optical parametric oscillator that is tunable over visible wavelengths with a few millijoules of energy.

Energy from the pump laser is absorbed by the sample molecules, which transfer the energy into the propane through non-radiative coupling. This energy induces localized heating in the propane and turns the metastable fluid into the gaseous phase at these sites. If these nucleation centers contain enough gas (>critical size) for the internal pressure to overcome the surface tension of the surrounding fluid a bubble will grow at that site. Since the energy for formation of the nucleation center comes from the laser pulse, bubble formation will occur at the laser induced nucleation centers well before wall nucleated boiling occurs. This allows a CCD camera with a micro-lens (55 mm focal length) to take a clear picture of the bubbles in the beam path. The bubbles are back-lit by an expanded and collimated laser diode beam so that the CCD sees the bubbles as dark circles with bright centers. Finally, the CCD video signal is captured by an asynchronous frame grabber and analyzed with a computer controlled image processing card. Baseline tests show that no bubbles are formed when the pump laser is fired before the pressure pulse or after the pressure pulse.

Proof of principle tests were conducted using crystal violet (CV) as a test sample. CV has a strong absorption in the visible region with a $6.6\times10^{-17}$ $cm^2$ cross section at 532 nm with a very small fluorescence yield. Thus, substantially all of the photon energy absorbed by the CV contributes to the formation of nucleation centers.

Although propane has very little absorption at 532 nm, even the purest grade propane that is commercially available has a significant number of bubble-forming impurities that produce some baseline bubble count. The baseline count is the limiting factor in the sensitivity of the bubble chamber spectrometer. Video frames of the resulting bubbles taken at delays of 150, 850, and 2300 μsec show that bubbles are produced only along the laser path; bubble size increases with increasing delay as the bubbles grow spontaneously in the superheated liquid.

Figure 3:
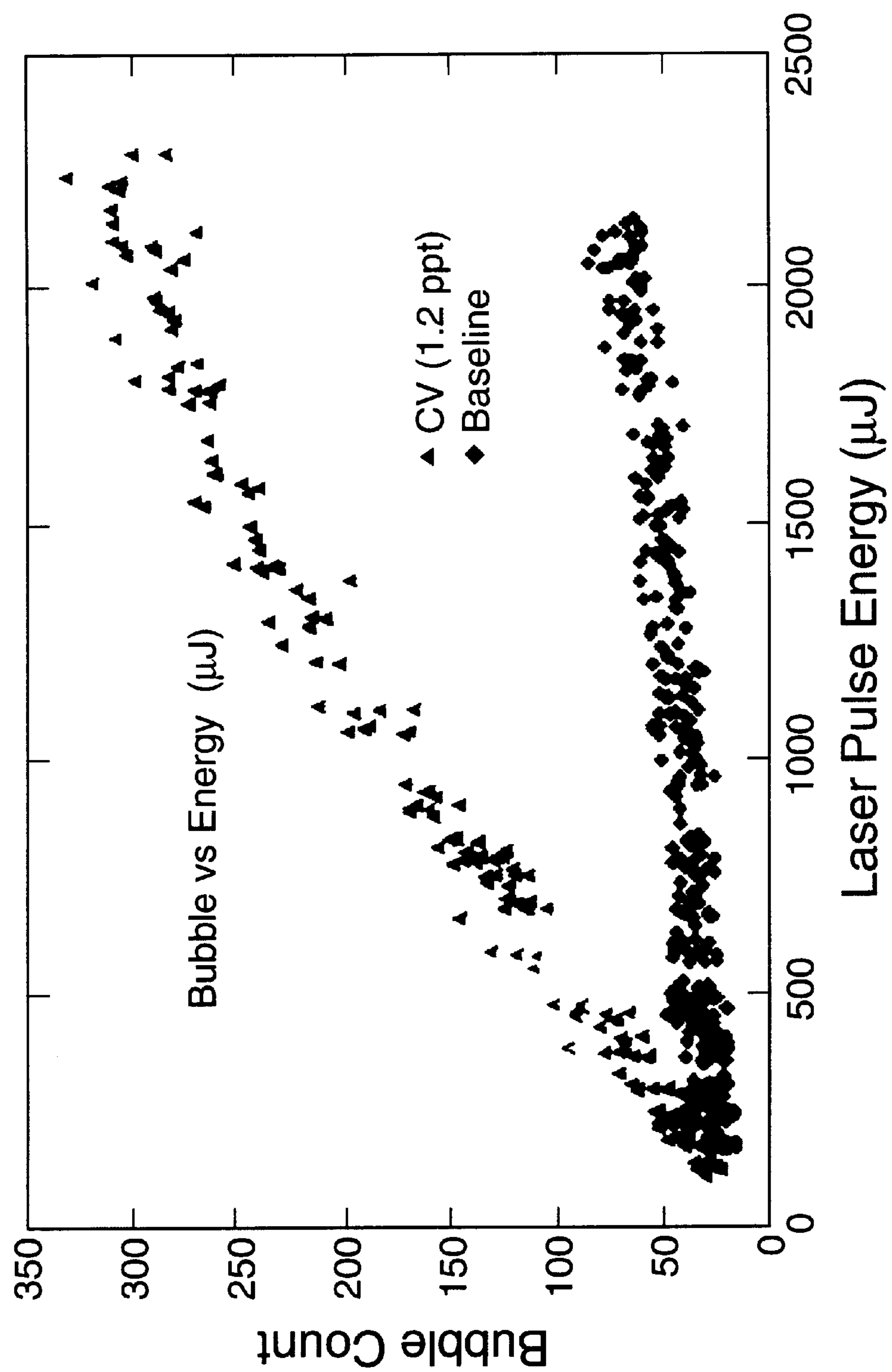
FIG. 3 graphically illustrates the sensitivity of the bubble chamber spectrometer for a particular analyte and solvent.

FIG. 3 graphically displays the number of bubbles produced as a function of laser pulse energy for pure propane and with an acetone/CV solution. This is the bubble chamber spectroscopy equivalent of an absorption versus light intensity plot of conventional spectroscopy. The sensitivity of the system down to 1.2 parts per trillion (ppt) CV is shown. To validate the use of acetone as a solvent, neat solutions of three grades of acetone were injected to determine the effect on the neat propane baseline count. HPLC and Reagent grade acetone did show a significant increase in the bubble count, but spectroscopic grade acetone was indistinguishable from the neat propane. The pressure pulse amplitude was held constant during the measurements because the pressure affects the number of bubbles that are produced. Both the neat propane and the propane with CV had a common threshold of 40 μJ for bubble formation, but then had different slopes for the concentrations of analyte. It will be appreciated that the sensitivity of the device can be increased to some extent by increasing the magnitude of the pressure pulse and by reducing impurities in the propane.

Figure 4:
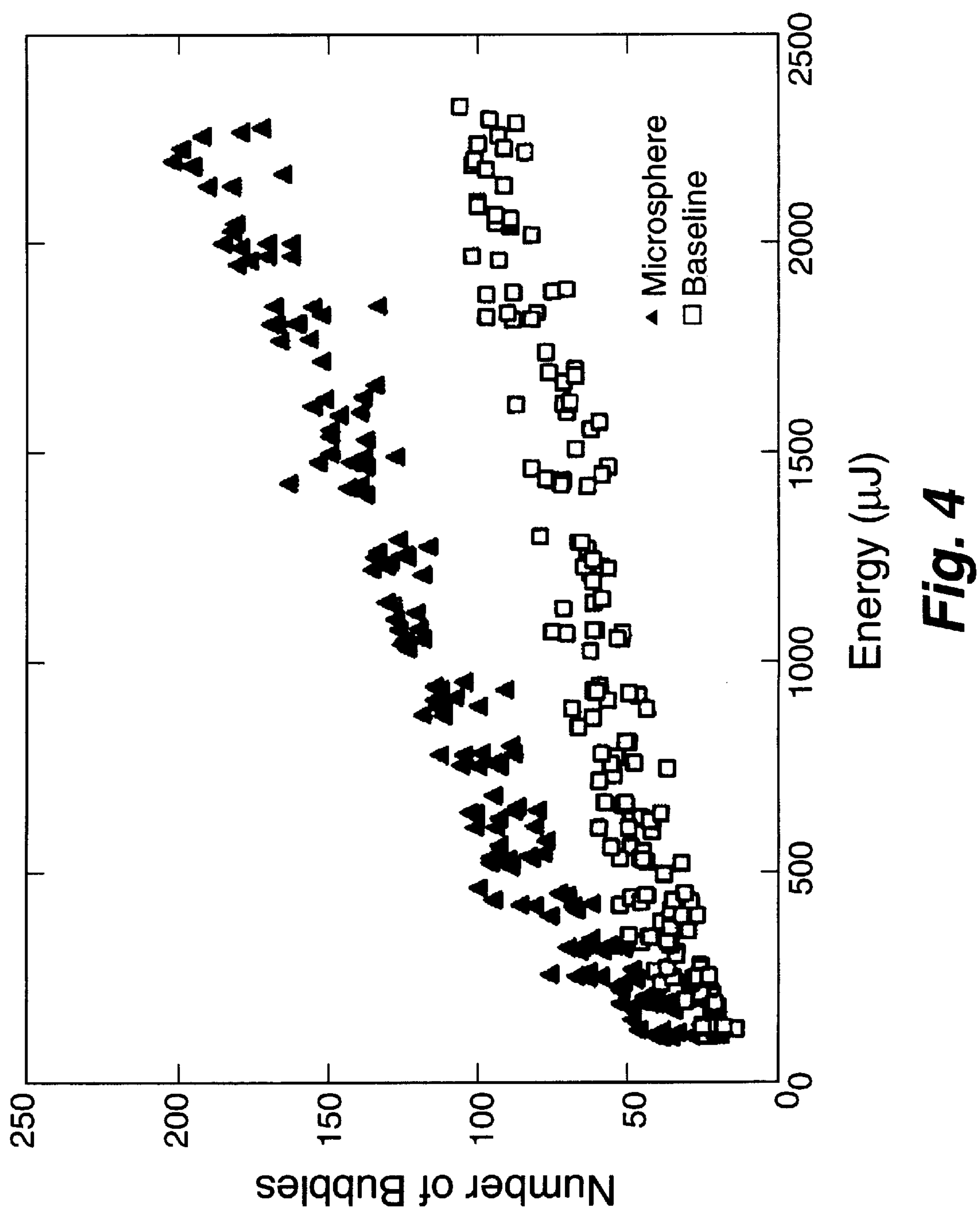
FIG. 4 graphically illustrates the sensitivity of the bubble chamber spectrometer for another particular analyte and solvent.

FIG. 4 graphically illustrates the application of bubble chamber spectroscopy to the detection of microspheres of 25 nm diameter in butanol. In this instance, the microspheres are clearly distinguished from the butanol baseline at laser pulse energies greater than about 1500 μJ.

Figure 5:
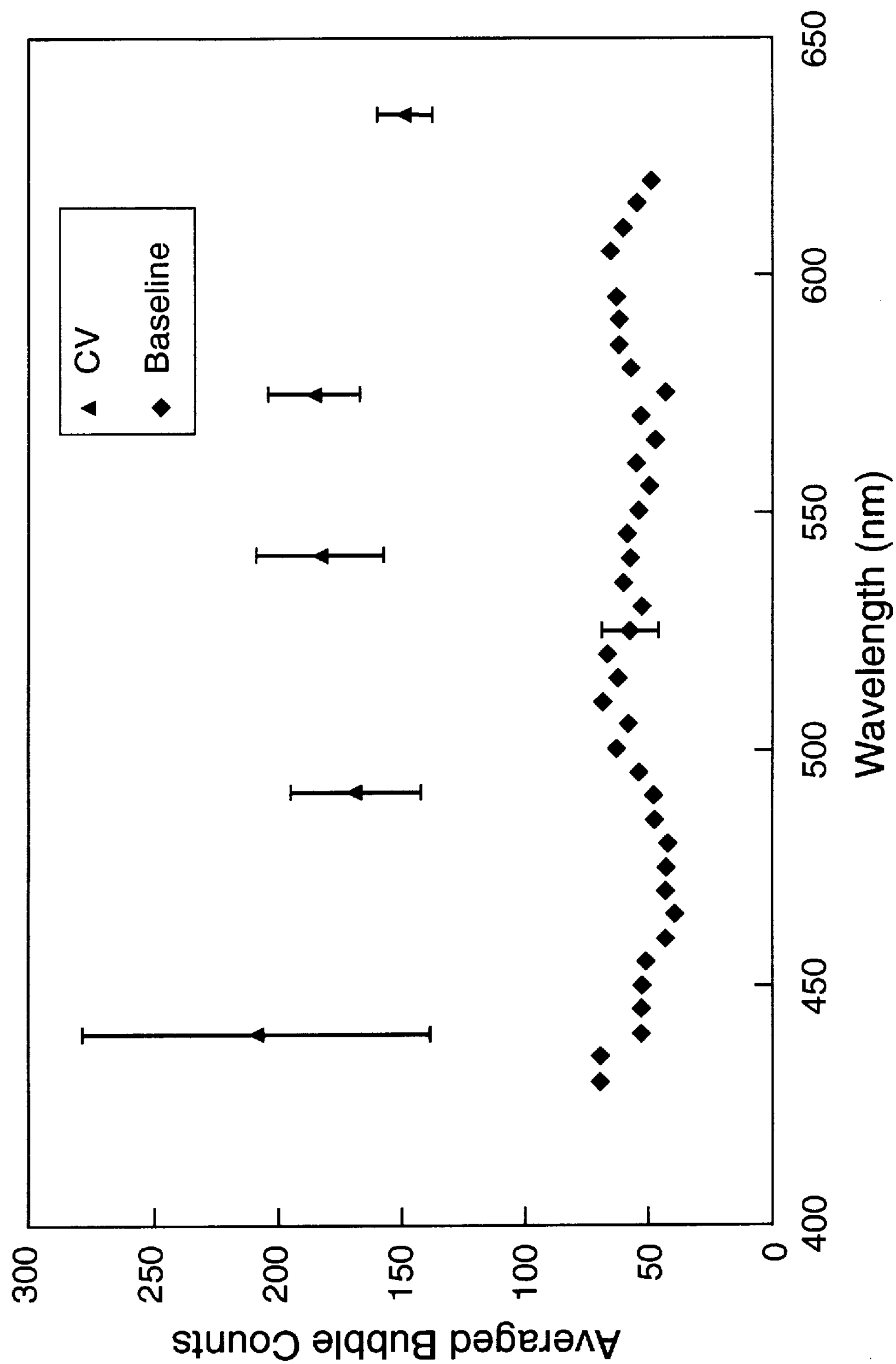
FIG. 5 graphically depicts the performance of the system shown in FIG. 1 at a variety of wavelengths to demonstrate the spectroscopic nature of the system.

FIG. 5 illustrates the output of the system described for FIG. 3 where the CV solution is illuminated at several wavelengths. The laser energy was 200 μJ from an optical parametric oscillator and the CV concentraction was 80 ppt. The error bars represent plus or minus one standard deviation. Approximately ten shots were averaged at each wavelength and the results were normalized to the energy per shot. Typically about 150 to 200 counts were obtained for the CV and 50 for the solvent background (pure propane). The results demonstrate that a spectral response may be obtained to further characterize the analyte.

A number of suitable solvents are available. In some chemical extraction processes, carbon dioxide is used to analyze chemicals in various matrices, and a sensitive analytical technique is required to look for the chemicals extracted into the carbon dioxide. Carbon dioxide at −40° C. has similar thermophysical properties as propane at room temperature and could be used as the superheated liquid solvent. Fluorocarbons have excellent transparency in the infrared region of the spectrum, which is important to a number of analytical applications.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A bubble chamber spectrometer comprising:

a bubble chamber for receiving a solution containing a solvent and an analyte;

a laser adapted to direct an output laser beam through said bubble chamber, wherein said laser has an output wavelength selected for absorbance by said analyte and transmittance by said solvent; and a video camera adapted to display passage of said laser beam along a path through said bubble chamber so that bubbles in said solvent arising from deposition of energy from said laser in said analyte are detected to characterize said analyte.

2. A bubble chamber spectrometer according to claim 1, further including a filter connected to said bubble chamber for removing particulate impurities from said solvent before introducing said analyte into said solvent.

3. A bubble chamber spectrometer according to claim 1, further including a light source for illuminating said path of said laser through said bubble chamber.

4. A bubble chamber spectrometer according to claim 1, further including an energy meter for measuring energy from said laser transmitted through said bubble chamber to characterize said laser.

5. A method for bubble chamber spectroscopy comprising the steps of:

passing a solvent containing an analyte into a bubble chamber;

reducing pressure in said bubble chamber to place said solvent in a superheated condition;

illuminating said solvent and said analyte with a laser to deposit energy in said analyte so that deposited energy in said analyte causes said solvent adjacent said analyte to form bubbles, wherein said laser has an output wavelength selected for absorbance by said analyte and transmittance by said solvent; and detecting said bubbles.

6. A method for bubble chamber spectroscopy according to claim 5, further including the steps of measuring energy from said laser transmitted through said bubble chamber: and detecting said bubbles as a function of said energy.

7. A method for bubble chamber spectroscopy according to claim 5, further including the step of establishing a baseline count for bubbles in said solvent.

* * * * *